United States Patent [19]

Ichii et al.

[11] Patent Number: 5,002,758
[45] Date of Patent: Mar. 26, 1991

[54] BATH PREPARATION COMPRISING FUMARIC ACID AND CARBONATE SALT

[75] Inventors: Yuji Ichii; Hirotaka Sato; Isamu Watanabe; Hidenori Yorozu, all of Tochigi, Japan

[73] Assignee: KAO Corporation, Tokyo, Japan

[21] Appl. No.: 324,885

[22] Filed: Mar. 17, 1989

[30] Foreign Application Priority Data

Mar. 17, 1988 [JP] Japan .................................. 63-64127
Mar. 18, 1988 [JP] Japan .................................. 63-65044

[51] Int. Cl.⁵ .......................... A61K 7/50; A61K 9/44
[52] U.S. Cl. ...................................... 424/44; 252/142; 252/174; 252/174.13; 252/174.14; 252/174.18; 252/174.21
[58] Field of Search .................... 252/142, 174, 174.13, 252/174.14, 90, 174.21, 174.18; 424/44, 78

[56] References Cited

U.S. PATENT DOCUMENTS 4,666,707  5/1987  Eguchi et al. .......................... 424/44

FOREIGN PATENT DOCUMENTS 106415  6/1984  Japan .

OTHER PUBLICATIONS

Chemical Abstracts, 101:16 (1984).
Patent Abstracts of Japan 10:383 (1986).
Patent Abstracts of Japan 12:75 (1988).

*Primary Examiner*—Prince E. Willis
*Attorney, Agent, or Firm*—Sughrue, Mion, Zinn, Macpeak & Seas

[57] ABSTRACT

A bathing preparation containing (a) fumaric acid, (b) a carbonate, (c) from 0.1 to 20% by weight, based on fumaric acid, of carboxymethyl cellulose, or an alkali metal salt thereof, having a viscosity of not higher than 2,000 cp in a 1.0% by weight aqueous solution at 25° C., or at least 0.2% by weight, based on fumaric acid, of polyethylene glycol, and (d) not less than 0.02% by weight and less than 0.1% by weight, based on fumaric acid, of a nonionic surface active agent having an HLB of 7 or more. The bathing preparation causes neither floating of fumaric acid or foaming when it is dissolved in a bath nor foaming after it is dissolved and the bath is agitated.

19 Claims, No Drawings

BATH PREPARATION COMPRISING FUMARIC ACID AND CARBONATE SALT

FIELD OF THE INVENTION

This invention relates to a bathing preparation containing fumaric acid and carbonates, which is added and dissolved in a hot bath. More particularly, it relates to a bathing preparation which does not substantially cause floating of fumaric acid or foaming when dissolved in a bath or foaming on agitation of the bath after it is dissolved therein.

BACKGROUND OF THE INVENTION

Bathing preparations generally comprise an inorganic salt mixture containing sodium sulfate (Glauber's salt), borax, sulfur, sodium chloride, carbonate, etc., having incorporated therein additives such as flavors, coloring materials, plant extracts, and organic acids. The bathing preparations function not only to impart flavors or color tones to baths but also to give moderate stimulation to the skin to activate blood circulation thereby relieving fatigue and promoting metabolism.

Implicit in these bathing preparations is a bubbling bathing preparation comprising a carbonate and an organic acid. The bathing preparations of this type produce bubbles of carbonic acid gas in a bath to promote relaxation or refreshment, and to make bathing pleasant.

The organic acid which can usually be incorporated into these bathing preparations include citric acid, succinic acid, malic acid, and tartaric acid. Fumaric acid, though cheaper than these organic acids, is unsuitable for use in bathing preparations because of its sparing water solubility. Hence, fumaric acid has been used in the form of sodium monofumarate or after being pretreated with a surface active agent by spray drying.

However, sodium monofumarate, in which one of the two carboxyl groups has been neutralized with sodium, must be used in a large quantity, thus increasing the cost. Although the method of spray drying fumaric acid together with a surface active agent is effective to inhibit floating of fumaric acid, the foam on the surface of water remains. If the amount of the surface active agent is decreased, floating of fumaric acid cannot be suppressed.

It has been proposed to coat fumaric acid by spraying a water-soluble high polymer comprising a homo- or copolymer of acrylic acid or a salt thereof having an average molecular weight of from 300 to 50,000 as disclosed in JP-A-60-169436 (the term "JP-A as used herein means an "unexamined published Japanese patent application").

However, this technique has a poor production efficiency and also entails high cost. Moreover, it is very difficult to completely remove water by drying.

In order to overcome these disadvantages associated with the use of fumaric acid, it has been proposed to add, to fumaric acid, from 1 to 20% by weight of one or more of sodium carboxymethyl cellulose, polyvinylpyrrolidone and water-soluble gelatin and from 0.1 to 0.5% by weight of a surface active agent having an HLB of 7 or more as disclosed in JP-A-59-106415.

The bathing preparation obtained by this method, however, still has disadvantages in that it causes foaming on agitating a bath after it is dissolved and the foam hardly disappears.

Therefore, there has not yet been developed a satisfactory technique to produce a bubbling bathing preparation containing fumaric acid which is free from any of the above-described disadvantages.

SUMMARY OF THE INVENTION

One object of this invention is to provide a bathing preparation containing fumaric acid and a carbonate which does not cause floating of fumaric acid or foaming of a bath.

In the light of the circumstances stated above, the inventors have conducted extensive investigations on a bathing preparation containing fumaric acid and a carbonate. As a result, it has now been found that the above object of this invention can be met by incorporating into the bathing preparation a specific amount of polyethylene glycol or carboxymethyl cellulose or an alkali metal salt thereof and a nonionic surface active agent having an HLB (hydrophile-lypophile balance) of 7 or more. The present invention has been completed based on this finding.

Accordingly, the present invention relates to a bathing preparation comprising (a) fumaric acid, (b) a carbonate, (c) from 0.1 to 20% by weight, based on fumaric acid, of carboxymethyl cellulose, or an alkali metal salt thereof, having a viscosity of not higher than 2,000 cp in a 1.0% by weight aqueous solution at 25° C. (hereinafter referred to as "CMC" or "CMC-M", respectively), or at least 0.2% by weight, based on fumaric acid, of polyethylene glycol (hereinafter referred to as "PEG"), and (d) not less than 0.02% by weight and less than 0.1% by weight, based on fumaric acid, of a nonionic surface active agent having an HLB of 7 or more.

DETAILED DESCRIPTION OF THE INVENTION

The carbonate which can be used in the bathing preparation of the present invention is not critical to the present invention. Examples thereof include sodium hydrogencarbonate, sodium carbonate, potassium hydrogencarbonate, potassium carbonate, calcium carbonate, magnesium carbonate, and sodium susquicarbonate. These carbonates can be used either individually or in combinations of two or more thereof.

In order to obtain improved preservability of the bathing preparation at high temperatures, it is preferable that at least 5% by weight, more preferably at least 10% by weight, of the total carbonates comprises alkali metal carbonates. When, in particular, the carboxymethyl cellulose or alkali metal salt thereof is used, it is preferable that at least 10% by weight of the total carbonates comprises alkali metal carbonates. If the proportion of alkali metal carbonates in the total carbonates is less than the above-recited lower limit, the preparation tends to undergo decomposition during preservation at high temperatures. This causes expansion of packages containing the same or reduction of the effective amount of carbonic acid gas which impairs the essential performance of the bubbling bathing preparations. The upper limit of the alkali metal carbonate proportion is not particularly critical, but if it exceeds 70% by weight, the dissolving speed tends to decrease.

The carbonate content in the preparation preferably ranges from 5 to 80% by weight, more preferably from 10 to 50% by weight.

If desired, the bathing preparation may contain other organic acids than fumaric acid. Examples thereof include citric acid, tartaric acid, malic acid, malonic acid, pyridone carboxylic acid, succinic acid, adipic acid, phosphoric acid, sodium citrate, sodium succinate, sodium fumarate, sodium phosphate, sodium adipate, etc. The total organic acid content preferably falls within a range of from 10 to 300% by weight, more preferably of from 30 to 150% by weight, based on the carbonate.

CMC or CMC-M which can be used in the present invention has a viscosity of not more than 2,000 cp, preferably not more than 1,000 cp, as measured in a 1.0% aqueous solution at 25° C. by means of a BM type rotational viscometer. If it has a viscosity exceeding 2,000 cp, it forms a highly water-retaining film when dissolved to produce masses, thereby giving an unpleasant feel to bathers.

The amount of the CMC or CMC-M to be added should be at least 0.1% by weight, preferably from 0.1 20% by weight, based on fumaric acid. If it is less than 0.1% by weight, floating of fumaric acid cannot be sufficiently inhibited.

PEG which can be used in the present invention preferably has an average molecular weight of from 2,000 to 10,000. It should be used in an amount of at least 0.2% by weight based on fumaric acid. If the amount is less than 0.2% by weight, floating of fumaric acid cannot be sufficiently inhibited. The upper limit of the amount of PEG is not particularly restricted but is preferably not more than 20% by weight.

The nonionic surface active agent having an HLB of 7 or more which can be used in the present invention is not critical thereto. Examples thereof include sucrose fatty acid esters, polyglycerin fatty acid esters, propylene glycol fatty acid esters, sorbitan fatty acid esters, polyoxyethylene sorbitan fatty acid esters, and polyoxyethylene glycol fatty acid esters. Preferred of these are sucrose fatty acid esters and polyglycerin fatty acid esters having an HLB of from 12 to 16.

The amount of the nonionic surface active agent to be added is at least 0.02% by weight and less than 0.1% by weight based on fumaric acid. If it is less than 0.02% by weight, floating of fumaric acid cannot be sufficiently inhibited. If it is 0.1% by weight or more, the preparation causes foaming on dissolving in a bath, and even after agitation, the foam hardly disappears.

In the case where the bathing preparation contains PEG as component (c), it is desirable that fumaric acid be present in such a state that it is treated with (c) PEG, and preferably (c) PEG and (d) the nonionic surface active agent. The term "in a state treated with" as used above means that component (c) or components (c) and (d) is or are present on the surface of fumaric acid. Such a state may be achieved by mixing all of the constituting components. In a preferred embodiment, such a state can be obtained by pretreating the surface of fumaric acid alone or, if desired, in combination with other organic acids with component (c) or components (c) and (d) beforehand and then mixing the pretreated fumaric acid with the carbonate and other components.

The above-described surface treatment of fumaric acid can be carried out in a known manner, such as spraying and immersion. It is preferable, however, that the treatment is effected by a hot-melt method, in which fumaric acid and the treating component(s) are melt-mixed by heating at 55° to 100° C., followed by cooling while stirring to powderize the mixture. In this case, it is desirable to use fumaric acid having a mean particle size of from 50 to 500 μm, and particularly from 100 to 500 μm.

The cooling and powderization of the molten mixture is preferably carried out while stirring in a fluidized bed having a paddle or a propeller blade. A preferred stirrer to be used has a circular cross section and is equipped with a rotating shaft in the center and a paddle or propeller blade at the bottom. The paddle or blade preferably has a diameter of 80% or more of the inner diameter of the fluidized bed.

The melt-mixing of fumaric acid and the treating component(s) may be carried out while elevating the temperature with warm water or warm air by the use of a jacketed mixer, a fluidized bed granulater, etc. It is more effective to use a vertical mixing machine, where the components are vigorously mixed and heated by the heat thus generated so that the treatment can be completed in a short time.

After the components are mixed at a temperature above the melting point of PEG, the mixture is transferred to a fluidized bed and cooled under conditions of from 2 to 15 m/sec in teams of the peripheral speed of the stirring blade and from 0.1 to 1.6 m/sec in teams of the superficial velocity of cooling air in a column.

If desired, the bathing preparation according to the present invention may further contain inorganic salts (e.g., sodium sulfate, magnesium sulfate, sodium chloride) in an amount of 0 to 20% by weight, preferably 0 to 10% by weight, based on the total components. For the purpose of improving effects of bathing, the bathing preparation may furthermore contain other additives commonly employed in bathing preparations, such as flavors, pigments, vitamins, effective ingredients of hot springs, proteolytic enzymes, sea weed extracts, sodium alginate, lanolin, silicones, crude drugs or extracts thereof, and so on.

It is possible to make carbonic acid gas exist in a bath in a dissolved state by appropriately selecting the ratio of the organic acids including fumaric acid to the carbonate so that the bath has a pH of from 5 to 7. It is expected, in this case, that the dissolved carbonic acid gas promotes blood circulation.

The form of the bathing preparations according to the present invention includes tablets, powders, granules, and the like, with tablets being preferred in view of increasing the amount of carbonic acid gas dissolved in hot water. The bathing preparations can contain additives necessary for formulation, such as vehicles and lubricants.

As described above, the bathing preparation of the present invention is free from floating of fumaric acid and foaming when dissolved in a bath. In addition, when a bath is agitated after the bathing preparation is dissolved therein, the foam caused by agitation rapidly disappears. The present invention thus makes it possible to utilize cheap fumaric acid in place of the conventionally employed expensive organic acids, e.g., citric acid, succinic acid, malic acid, and tartaric acid, to thereby decrease the production cost.

Further, the bathing preparation of the present invention produces bubbles of carbonic acid gas in a bath, which leads to promotion of blood circulation, through appropriate selection of the ratio of the organic acid to the carbonate.

The present invention is now illustrated in greater detail by way of the following Examples, but it should be understood that the present invention is not deemed to be limited thereto.

EXAMPLE 1

The components shown in Table 1 below were mixed, and tablets each weighing 50 g were punched out. The resulting bathing preparation (50 g) was thrown into a bath tub (910×710 cm) filled with 150 l of water at 40° C.

Floating of fumaric acid and foaming of a bath on dissolving the bathing preparation and foaming of the bath after dissolving the bathing preparation and agitating the bath were evaluated and rated as follows.

(1) Floating of Fumaric Acid:

The bathing preparation was thrown into a bath, and the time required for disappearance of the float was measured and evaluated according to the following rating system.

Excellent: No floating was observed at all.

Good: The float disappeared within less than 1 minute from the throwing into a bath.

Moderate: The float disappeared after 1 minute and within less than 3 minutes from the throwing into a bath.

Bad: The float remained on the surface of water for 3 minutes or more from the throwing into a bath.

(2) Foaming

Immediately after the bathing preparation was completely disintegrated in a bath, the proportion of the area of the water surface on which the foam remained based on the entire area of the water surface was measured and evaluated according to the following rating system.

Good: No foaming was observed.

Moderate: The area of the foaming surface was less than 10%.

Bad: The area of the foaming surface was 10% or more.

(2) Foaming After Agitation:

After the bathing preparation was completely dissolved in a bath, the bath was agitated with five strokes of a bowl having a diameter of about 30 cm. The time required for disappearance of the foam caused by the agitation was measured and evaluated according to the following rating system.

Good: 5 seconds or less.

Moderate: More than 5 seconds and up to 1 minute.

Bad: More than 1 minute.

The results obtained are shown in Table 1.

TABLE 1

| | Run No. | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Components (% by weight): | | | | | | | | | | | | |
| Sodium hydrogencarbonate | 42.996 | 44.930 | 42.980 | 39.985 | 42.950 | 42.980 | 55.98 | 55.98 | 55.98 | 55.96 | 55.98 | 55.98 |
| Sodium carbonate | 15.000 | 15.000 | 15.000 | 14.000 | 15.000 | 15.000 | — | — | — | — | — | — |
| Fumaric acid | 40.000 | 40.000 | 40.000 | 42.000 | 40.000 | 40.000 | 40.00 | 40.00 | 40.00 | 40.00 | 40.00 | 40.00 |
| PEG (average mol. wt: 6,000) | 2.000 | 0.050 | 2.000 | 4.000 | 2.000 | 2.000 | — | — | — | — | 4.00 | 4.00 |
| Polyvinylpyrrolidone | — | — | — | — | — | — | — | 4.00 | — | 4.00 | — | — |
| CMC-Na* | — | — | — | — | — | — | 4.00 | — | — | — | — | — |
| Water-soluble gelatin | — | — | — | — | — | — | — | — | 4.00 | — | — | — |
| Sucrose fatty acid ester (HLB: 16) | 0.004 | 0.020 | 0.020 | 0.015 | 0.050 | — | 0.02 | 0.02 | 0.02 | 0.04 | 0.02 | — |
| Polyglycerin fatty acid ester (HLB: 15) | — | — | — | — | — | 0.020 | — | — | — | — | — | 0.02 |
| Floating of Fumaric Acid | bad | bad | good | good | good | good | bad | bad | bad | good | good | good |
| Foaming | good | good | good | good | bad | good | good | good | good | good | good | good |
| Foaming after agitation | good | good | good | good | bad | good | good | good | good | bad | good | good |

Note:
*Viscosity in a 1.0 wt % aqueous solution at 25° C. was 3,000 cp (BM viscometer)

From the results of Table 1, it can be seen that if the amount of the nonionic surface active agent having an HLB of 7 or more is less than 0.02% by weight based on fumaric acid, floating of fumaric acid cannot be inhibited as shown in Run No. 1, and if it is 0.1% by weight or more, foaming occurs as shown in Run No. 5. It can also be seen that if the amount of PEG is less than 0.2% by weight based on fumaric acid, floating of fumaric acid cannot be inhibited as shown in Run No. 2.

In Run Nos. 3, 4 and 6, which fall within the scope of the present invention, floating of fumaric acid, foaming, and foaming after agitation were not observed.

Run No. 10 demonstrates that the method of JP-A-59-106415 fails to inhibit foaming after agitation. In order to prevent such foaming after agitation, if the amount of the surface active agent is decreased to less than 0.1% by weight as in Run Nos. 7, 8, and 9, the floating of fumaric acid cannot be inhibited.

In Run Nos. 11 and 12 according to the present invention, floating of fumaric acid, foaming, and foaming after agitation were not observed.

EXAMPLE 2

Fumaric acid, PEG, and a nonionic surface active agent (a sucrose fatty acid ester and/or polyglycerin fatty acid ester) in the amounts shown in Table 2 below were mixed by stirring in a Henschel mixer (FM 20B, manufactured by Mitsui Miike Kakoki K.K.) at 1800 rpm until the inner temperature was raised up to 70° C. The mixture was then cooled while stirring for powderization to obtain surface-treated fumaric acid.

The thus treated fumaric acid was mixed with the carbonate component shown in Table 2 and punched out to obtain tablets of a bathing preparation. The resulting bathing preparation was evaluated in the same manner as in Example 1. The results obtained are shown in Table 2.

TABLE 2

| | Run No. 13 | Run No. 14 | Run No. 15 | Run No. 16 | Run No. 17 |
|---|---|---|---|---|---|
| Components (% by weight): | | | | | |
| Sodium hydrogencarbonate | 42.980 | 39.985 | 42.980 | 55.980 | 55.980 |

TABLE 2-continued

|  | Run No. 13 | Run No. 14 | Run No. 15 | Run No. 16 | Run No. 17 |
| --- | --- | --- | --- | --- | --- |
| Sodium carbonate | 15.000 | 14.000 | 15.000 | — | — |
| Fumaric acid | 40.000 | 42.000 | 40.000 | 40.000 | 40.000 |
| PEG (average mol. wt.: 6,000) | 2.000 | 4.000 | 2.000 | 4.000 | 4.000 |
| Sucrose fatty acid ester (HLB: 16) | 0.020 | 0.015 | — | 0.020 | — |
| Polyglycerin fatty acid ester (HLB: 15) | — | — | 0.020 | — | 0.020 |
| Floating of Fumaric Acid | excellent | excellent | excellent | excellent | excellent |
| Foaming | good | good | good | good | good |
| Foaming after agitation | good | good | good | good | good |

EXAMPLE 3

The components shown in Table 3 were mixed and punched out to obtain tablets each weighing 50 g. Each of the tablets was wrapped air-tight in an aluminum laminate film and preserved at room temperature or 50° C. for 20 days.

After the preservation, the tablet was thrown into a bath tub (910×710 cm) filled with 150 l of water at 40° C. Floating of fumaric acid and foaming, and foaming after dissolving and agitation were evaluated in the same manner as in Example 1. Further, the time required from the throwing of the tablet into the bath up to complete disintegration of the tablet was measured, and expansion of the package was evaluated as follows. The results obtained are shown in Table 3.

(4) Expansion of Package:

The volume of each sample was measured before and after the preservation, and the change in volume was rated as follows.

Acceptable: The change in volume was less than 5 ml.

Unacceptable: The change in volume was 5 ml or more.

TABLE 3

|  | Run No. 18 | Run No. 19 | Run No. 20 |
| --- | --- | --- | --- |
| Component (% by weight): |  |  |  |
| Sodium hydrogencarbonate | 42.99 | 57.99 | 51.99 |
| Sodium carbonate | 15.00 | — | 6.00 |
| Fumaric acid | 40.00 | 40.00 | 40.00 |
| PEG (average molecular weight: 6000) | 2.00 | 2.00 | 2.00 |
| Sucrose fatty acid ester (HLB: 16) | 0.01 | 0.01 | 0.01 |
| Preserved at room temperature: |  |  |  |
| Floating of fumaric acid | good | good | good |
| Foaming | good | good | good |
| Time required for distintegration | 7 min. | 7 min. | 8 min. |
|  | 54 sec. | 46 sec. | 7 sec. |
| Foaming after agitation | good | good | good |
| Expansion of package | acceptable | acceptable | acceptable |
| Preserved at 50° C.: |  |  |  |
| Floating of fumaric acid | good | bad | good |
| Foaming | good | good | good |
| Foaming after agitation | good | good | good |
| Expansion of package | acceptable | unacceptable | acceptable |

As can be seen by comparing Run No. 19 with Run Nos. 18 and 20, bathing preparations containing sodium carbonate in a proportion of 5% by weight or more based on the total carbonate exhibit superior stability on preservation at high temperatures while retaining the essential effects to prevent floating of fumaric acid, foaming, and foaming after agitation.

EXAMPLE 4

Eight kilograms of fumaric acid, 400 g of PEG (average molecular weight: 6000), and 4.0 g of a sucrose fatty acid ester (HLB: 16) were mixed in a Henschel mixer (FM 20B) at 1800 rpm until the inner temperature was elevated up to 70° C. Thereafter, tap water of about 22° C. was made to circulate through the jacket of the mixer, and the mixture was further stirred at 600 rpm until the inner temperature fell to 35° C.

The resulting mixture (420.2 kg, consisting of 400 kg of fumaric acid, 20 kg of PEG, and 0.2 kg of the sucrose fatty acid ester), 429.8 kg of sodium hydrogencarbonate, and 150 kg of sodium carbonate (amounting to 1000 kg in total) were mixed in a NAUTA-mixer (volume: 2.5 $m^3$; manufactured by Hosokawa Micron K.K.). After passing through a 16 mesh sieve to remove coarse grains, the mixture was continuously punched out by means of a tableting machine (DC-WD, manufactured by Machina K.K.) to obtain tablets each weighing 50 g. During the continuous punching, the surface of the tablets were examined for unevenness, which indicated that the mixture sticked to the pestle. As a result, there was observed no sticking to the pestle even after 4500 shots.

Separately, tablets were obtained in the same manner as described above, except that fumaric acid was not pretreated and all the components were directly mixed in a NAUTA-mixture. In this case, there was observed sticking of the mixture to the pestle after 4,500 shots. If sticking to a pestle takes place, the pestle should be washed so that the productivity of tableting is reduced.

From these results, it is apparent that the productivity of tableting can be improved by using fumaric acid pretreated with PEG and the nonionic surface active agent by a hot-melt method.

EXAMPLE 5

Four kilograms of fumaric acid, 4.0 kg of succinic acid, 400 g of PEG (average molecular weight: 6000), and 4.0 g of a sucrose fatty acid ester (HLB: 16) were mixed in a Henschel mixer (FM 20B) at 1800 rpm until the inner temperature rose to 70° C., and the stirring was further continued at 600 rpm until the temperature fell to 35° C.

A mixture (1000 kg) consisting of 420.2 kg of the above obtained mixture (consisting of 200 kg of fumaric acid, 200 kg of succinic acid, 20 kg of PEG, and 0.2 kg of the sucrose fatty acid ester), 429.8 kg of sodium hydrogencarbonate, and 150 kg of sodium carbonate was mixed in a NAUTA-mixer (volume: 2.5 $m^3$; manufactured by Hosokawa Micron K.K.). After passing through a 16 mesh sieve to remove coarse grains, the mixture was continuously punched out to obtain tablets each weighing 50 g. Even after 4500 shots, no sticking to the pestle was observed.

Each tablet was wrapped air-tight in an aluminum laminate film and preserved at room temperature or 50° C. for 20 days. After the preservation, the tablet was thrown into a bath tub (910×710 cm) filled with 150 l of water at 40° C. The floating and foaming on dissolving and foaming after agitation were evaluated in the same manner as in Example 1, and expansion of the package was evaluated in the same manner as in Example 3. As a result, the bathing preparation was found free from any problem in any case.

EXAMPLE 6

The components shown in Table 4 were mixed and punched out to prepare tablets each weighing 50 g. The tablet was poured into a bath tub (910×710 cm) filled with 150 l of water at 40° C. The floating of fumaric acid and foaming on dissolving and foaming after agitation were evaluated in the same manner as in Example 1, except that the floating of fumaric acid was rated as follows.

Good: The float disappeared within less than 30 seconds from the throwing.

Bad: The float remained on the surface of the water for 3 minutes or more from the throwing.

The results obtained are shown in Table 4.

TABLE 4

| Components (% by weight): | 1 | 2 | 3 | 4 | 5 | 6 | 7 | 8 | 9 | 10 | 11 | 12 |
|---|---|---|---|---|---|---|---|---|---|---|---|---|
| Sodium hydrogencarbonate | 44.496 | 44.950 | 44.480 | 42.985 | 43.950 | 44.480 | 42.96 | 42.98 | 42.98 | 42.98 | 42.98 | 42.98 |
| Sodium carbonate | 15.000 | 15.000 | 15.000 | 14.000 | 15.000 | 15.000 | 15.00 | 15.00 | 15.00 | 15.00 | 15.00 | 15.00 |
| Fumaric acid | 40.000 | 40.000 | 40.000 | 42.000 | 40.000 | 40.000 | 40.00 | 40.00 | 40.00 | 40.00 | 40.00 | 40.00 |
| CMC-Na* | 0.500 | 0.030 | 0.500 | 1.000 | 1.000 | 0.500 | — | — | — | — | 2.00 | 2.00 |
| CMC-Na** | — | — | — | — | — | — | — | 2.00 | — | — | — | — |
| Polyvinylpyrrolidone | — | — | — | — | — | — | 2.00 | — | 2.00 | — | — | — |
| Water-soluble gelatin | — | — | — | — | — | — | — | — | — | 2.00 | — | — |
| Sucrose fatty acid ester (HLB: 16) | 0.004 | 0.020 | 0.020 | 0.015 | 0.050 | — | 0.04 | 0.02 | 0.02 | 0.02 | 0.02 | — |
| Polyglycerin fatty acid ester (HLB: 15) | — | — | — | — | — | 0.020 | — | — | — | — | — | 0.02 |
| Floating of Fumaric Acid | bad | bad | good | good | good | good | good | bad | bad | bad | good | good |
| Foaming | good | good | good | good | bad | good | good | good | good | good | good | good |
| Foaming after agitation | good | good | good | good | bad | good | bad | good | good | good | good | good |

Note
*Viscosity in a 1.0 wt % aqueous solution at 25° C. was 300 cp (BM type viscometer)
**Viscosity in a 1.0 wt % aqueous solution at 25° C. was 3,000 cp (BM type viscometer)

It can be seen from Table 4 that if the amount of the nonionic surface active agent having an HLB of 7 or more is less than 0.02% by weight based on fumaric acid as in Run No. 1, floating of fumaric acid cannot be inhibited and that if the amount of the surface active agent is 0.1% by weight or more as in Run No. 5, foaming occurs.

Run No. 2 shows that floating of fumaric acid cannot be inhibited if the amount of CMC-M is less than 0.1% by weight based on fumaric acid, i.e., floating of fumaric acid cannot be suppressed.

In Run Nos. 3, 4, and 6 according to the present invention, floating of fumaric acid, foaming, and foaming after agitation were not observed.

Run No. 7 shows that the method of JP-A-59-106415 fails to inhibit foaming after agitation of a bath. In order to prevent such foaming caused by agitation, if the amount of the nonionic surface active agent having an HLB of 7 or more is decreased to less than 0.1% by weight based on fumaric acid as in Run Nos. 8, 9, and 10, floating of fumaric acid can be no longer inhibited.

In Run Nos. 11 and 12 according to the present invention, floating of fumaric acid, foaming, and foaming after agitation were not observed.

While the invention has been described in detail and with reference to specific embodiments thereof, it will be apparent to one skilled in the art that various changes and modifications can be made therein without departing from the spirit and scope thereof.

What is claimed is:

1. A bathing preparation comprising:

(a) fumaric acid (b) a carbonate, (c) carboxymethyl cellulose, or an alkali metal salt thereof, having a viscosity or not higher than 2,000 cp in a 1.0% by weight aqueous solution at 25° C., in an amount of from 0.1 to 20% by weight based on the fumaric acid, or at least 0.2% by weight, based on the fumaric acid, of polyethylene glycol, and (d) a nonionic surface active agent having an HLD value of 7 or more in an amount of not less than 0.02% by weight and less than 0.1% by weight, based on the fumaric acid, wherein the fumaric acid is present in a amount from 10–300% by weight based on the carbonate, and the carbonate is present in an amount of from 5 to 80% by weight based on the total weight of the bathing preparation.

2. The bathing preparation as claimed in claim 1, wherein said fumaric acid is contacted with at least 0.2% by weight of polyethylene glycol so that the polyethylene glycol is on the surface of the fumaric acid.

3. The bathing preparation as claimed in claim 1, wherein said bathing preparation is obtained by contacting the fumaric acid with at least 0.2% by weight of polyethylene glycol so that the polyethylene glycol is on the surface of the fumaric acid and then mixing the thus pretreated fumaric acid with components (b) and (d).

4. The bathing preparation as claimed in claim 1, wherein said fumaric acid has an average particle size of from 90 to 500 μm.

5. The bathing preparation as claimed in claim 3, wherein said contacting is carried out by melt-mixing fumaric acid and polyethylene glycol and cooling the molten mixture while stirring to powderize.

6. The bathing preparation as claimed in claim 1, wherein said fumaric acid is contacted with at least 0.2 by weight of polyethylene glycol and not less than 0.02% by weight and less than 0.1% by weight of the nonionic surface active agent having an HLB of 7 or more, so that the polyethylene glycol and the nonionic surface active agent are on the surface of the fumaric acid.

7. The bathing preparation as claimed in claim 1, wherein said bathing preparation is obtained by contacting the fumaric acid with at least 0.2% by weight of polyethylene glycol and not less that 0.02% by weight and less than 0.1% by weight of the surface active agent having an HLB of 7 or more, so that the polyethylene glycol and the nonionic surface active agent are on the surface of the fumaric acid and then mixing the thus pretreated fumaric acid with component (b).

8. The bathing preparation as claimed in claim 7, wherein said fumaric acid has an average particle size of from 50 to 500 μm.

9. The bathing preparation as claimed in claim 7, wherein said contacting is carried out by melt-mixing fumaric acid, polyethylene glycol, and the nonionic surface active agent having an HLB of 7 or more and cooling the molten mixture while stirring to powderize.

10. The bathing preparation as claimed in claim 1, wherein component (b) comprises not less than 5% by weight of an alkali metal salt of carbonic acid based on the total of component (b).

11. The bathing preparation as claimed in claim 10, wherein component (b) comprises not less than 10% by weight of an alkali metal salt of carbonic acid based on the total of component (b).

12. The bathing preparation as claimed in claim 3, wherein component (b) comprises not less than 5% by weight of an alkali metal salt of carbonic acid based on the total of component (b).

13. The bathing preparation as claimed in claim 7, wherein component (b) comprises not less than 5% by weight of an alkali metal salt of carbonic acid based on the total of component (b).

14. The bathing preparation as claimed in claim 1, wherein said carboxymethyl cellulose or an alkali metal salt thereof has a viscosity of not higher than 1000 cp.

15. The bathing preparation as claimed in claim 1, wherein said polyethylene glycol has an average molecular weight of from 2000 to 10000.

16. The bathing preparation as claimed in claim 1, wherein said nonionic surface active agent is a sucrose fatty acid ester having an HLB of from 12 to 16 or a polyglycerin fatty acid ester having an HLB of from 12 to 16.

17. The bathing preparation as claimed in claim 1, wherein said carbonate is selected from the group consisting of sodium hydrogencarbonate, sodium carbonate, potassium hydrogencarbonate, potassium carbonate, calcium carbonate, magnesium carbonate and sodium sesquicarbonate.

18. The bathing preparation as claimed in claim 1, wherein said nonionic surface active agent is selected from the group consisting of sucrose fatty acid esters, polyglycerin fatty acid esters, propylene glycol fatty acid esters, sorbitan fatty acid esters, polyoxyethylene sorbitan fatty acid esters and polyoxyethylene glycol fatty acid esters.

19. The bathing preparation as claimed in claim 1, wherein the fumaric acid is present in an amount of from 30 to 150% by weight based on the carbonate, and the carbonate is present in an amount of from 20 to 50% by weight based on the total weight of the bathing preparation.

* * * * *